United States Patent
Chae et al.

(10) Patent No.: US 6,652,099 B2
(45) Date of Patent: Nov. 25, 2003

(54) APPARATUS FOR FOCUSING IRIS IMAGES OF BOTH EYES

(75) Inventors: Jang Jin Chae, Kyounggi-do (KR); Seung Gi Min, Seoul (KR)

(73) Assignee: LG Electronics, Inc., Seoul (KR)

( * ) Notice: Subject to any disclaimer, the term of this patent is extended or adjusted under 35 U.S.C. 154(b) by 81 days.

(21) Appl. No.: 09/988,063

(22) Filed: Nov. 16, 2001

(65) Prior Publication Data

US 2002/0057439 A1 May 16, 2002

(30) Foreign Application Priority Data

Nov. 16, 2000 (KR) .................................... 2000-68218

(51) Int. Cl.[7] ................................................ A61B 3/10
(52) U.S. Cl. ........................................ 351/204; 382/117
(58) Field of Search ................................ 351/204, 205, 351/206, 208, 210, 220, 221; 382/117, 128, 324

(56) References Cited

U.S. PATENT DOCUMENTS 5,471,542 A * 11/1995 Ragland ..................... 351/208

* cited by examiner

Primary Examiner—George Manuel
(74) Attorney, Agent, or Firm—Fleshner & Kim, LLP

(57) ABSTRACT

The invention relates to an iris recognition system, and more particularly, to an apparatus for approaching the iris images of the both eyes most adjacent within a range beyond which the iris images overlap each other in an iris recognition system using all of the iris images of the both eyes at the same time. The iris recognition system using all of the iris images of the both eyes at the same time adopts an apparatus for narrowing the distance between the iris images of the both eyes acquired in CCD images when the iris images are obtained through photographing the iris images of the both eyes are photographed. The apparatus of the invention comprises iris image focusing means for converting an incident path, whereby the distance between the iris images of the both eyes is narrowed on an optical path along which eye images of the user are focused to a camera, in which the focusing means can be an angled reflector with one side being inclined at an angle about the center.

13 Claims, 4 Drawing Sheets

APPARATUS FOR FOCUSING IRIS IMAGES OF BOTH EYES

BACKGROUND OF THE INVENTION

1. Field of the Invention

The present invention relates to an iris recognition system, and more particularly, to an apparatus for focusing iris images of both eyes in an iris recognition system using both irises of both eyes, by which the iris images of the mutually distanced both eyes are approached to reduce the distance between the two iris images in obtaining the iris images.

Meanwhile, the invention can be applied to an iris recognition system of both eyes which extracts the iris images of the both eyes including both images of the both eyes and compares the extracted iris images of the both eyes to a previously registered image data base of both eye iris images to execute credibility judgment and authentication of a recognizee.

In particular, the invention relates to an apparatus for focusing iris images of both eyes which can focus the iris images of the both eyes adjacent using a reflector angled at a predetermined degree to narrow the distance between the both eyes in the acquired both eye iris images so that unnecessary image information can be reduced and iris information necessary for recognition can be acquired in a sufficient amount.

2. Description of the Related Art

As well known, conventional systems for security, guard and identity authentication include contacting or non-contacting card systems. Further, systems have been popularized for authenticating identity and allowing or rejecting entry into specific spaces or access to specific information through recognizing fingerprints or an iris of a person.

Among these, the iris recognition system has an advantage that more precise recognition can be obtained with a higher recognition rate over the fingerprints recognition. In the iris recognition system, a specific pattern is processed into data using an image processing technique from an iris image photographed by a video camera and then compared to pre-registered iris data in authenticating a person.

FIG. 1 shows a configuration of a general iris recognition system. The operation of the iris recognition system will be described in reference to FIG. 1 as follows.

When a user approaches the iris recognition system, a distance-measuring sensor 109 measures a distance from the user 109. The distance measured like this is sent to a control unit 105 via a driver 107 to judge if the measured distance is within an operational range that the system can be operated.

If the user is within the operational range, a control signal is sent to the driver 107 to prepare for extracting an iris image. The driver 107 sends an active signal to the outer indicator 108 to inform the user that the system is operating, and when the user accordingly places an eye at an optical axis of a camera 103 through an optical window 101, a cold mirror 102 shields visual light while allowing infrared light to pass therethrough. A region where an iris is supposed to be placed is indicated so that the user can confirm if the eye is placed at the optical axis of the camera 103.

Again, the control unit 105 accepts a value of the measured distance from the distance measuring sensor 109 to the user, and calculates zoom and focus values of the camera 103 using the measured distance to execute zoom-in/zoom-out and focusing control. Then, the control unit 105 regulates the intensity of an illuminating unit 106 via a driver 107 according to the measured distance, and then photographs the iris image via the camera 103. The photographed iris image is signal processed in a frame grabber 104 corresponding to iris image analysis, and the control unit 105 executes iris recognition using information of the processes iris image to determine if to authenticate the user.

In such an iris recognition system, performance thereof is determined by speed and precision of iris recognition.

However, when recognition is carried out using the iris of only one eye, the iris image for recognition should be obtained in a large size in order to acquire sufficient information with only one iris. Therefore, the video camera for iris recognition is required to have a considerable level of zooming and focusing functions, in which the iris image should be photographed in a sufficient size while the zooming function is used to adjust a focus. Also, since the iris of only one eye is used, an operation area of the user should be set adjacent to the lens in order to acquire a sufficient level of iris image, and focusing is difficult.

Due to such reasons, the conventional iris recognition system using the iris image of one eye has been required to allocate a number of components and algorithms for realizing an automatic focusing function.

Further, with regard to comparative search time for iris recognition, the degree of rotation of the iris is not known when the iris of only one eye is used so that a comparative search is executed considering rotation of the iris thereby consuming a long search time. This acts as a great obstacle in obtaining the iris recognition system in real time.

Therefore, those problems can be solved if iris images of both eyes can be used in executing user authentication.

In other words, when all the iris images of the both eyes are used at the same time, desired iris images can be obtained substantially without using the zooming function, and thus incurring an iris image acquiring apparatus to be simplified.

Further, the error rate can be lowered since authentication is obtained only if iris information from the both eyes are identical using all the irises of the both eyes, and the degree of rotation of the irises can be easily obtained allowing the comparative search time of information to be shortened since so that a basis can be provided for executing iris recognition substantially in real time.

In simultaneously using the iris images of the both eyes like this, unnecessary information or glabella information unnecessary for iris recognition is acquired between the iris images of the both eyes photographed by a CCD camera, and thus such information has been an obstruction in processing iris information which is necessary in practice.

SUMMARY OF THE INVENTION

According to an aspect of the invention, it is provided an apparatus for focusing iris images of both eyes in a system which executes iris recognition by using the iris images of the both eyes of a user, the apparatus comprising: iris image focusing means for converting an incident path, whereby the distance between the iris images of the both eyes is narrowed on an optical path along which eye images of the user are focused to a camera. In the apparatus of the invention, the focusing means is an angled reflector with one side being inclined at an angle about the center.

According to another aspect of the invention, it is provided an apparatus for focusing iris images of both eyes comprising: a reflector inclined at an angle about a reference position for setting the iris images of the both eyes with reflection angles different with each other when the iris images of the both eyes are inputted; a lens for refracting the iris images reflected from the reflector; and a photographing device for converting optical signals containing the iris images into electric signals.

According to other aspect of the invention it is provided a method for recognizing iris images of both eyes comprising the following step of: reflecting lights inputted as the iris images of the both eyes in different angles for being narrowed, wherein all of the iris images of the both eyes are used in user authentication through focusing, photographing and authentication, whereby the distance between the iris images of the both eyes formed on a photographing device is narrowed.

According to the invention, in the iris recognition system using the both eyes, the distance between the two eyes or the distance between the iris images formed on the photographing device can be reduced so that the iris images can be acquired larger and more precise.

DETAILED DESCRIPTION OF THE PREFERRED EMBODIMENT

The following Detailed Description will present a discussion of preferred embodiments of the invention.

Figure 1:
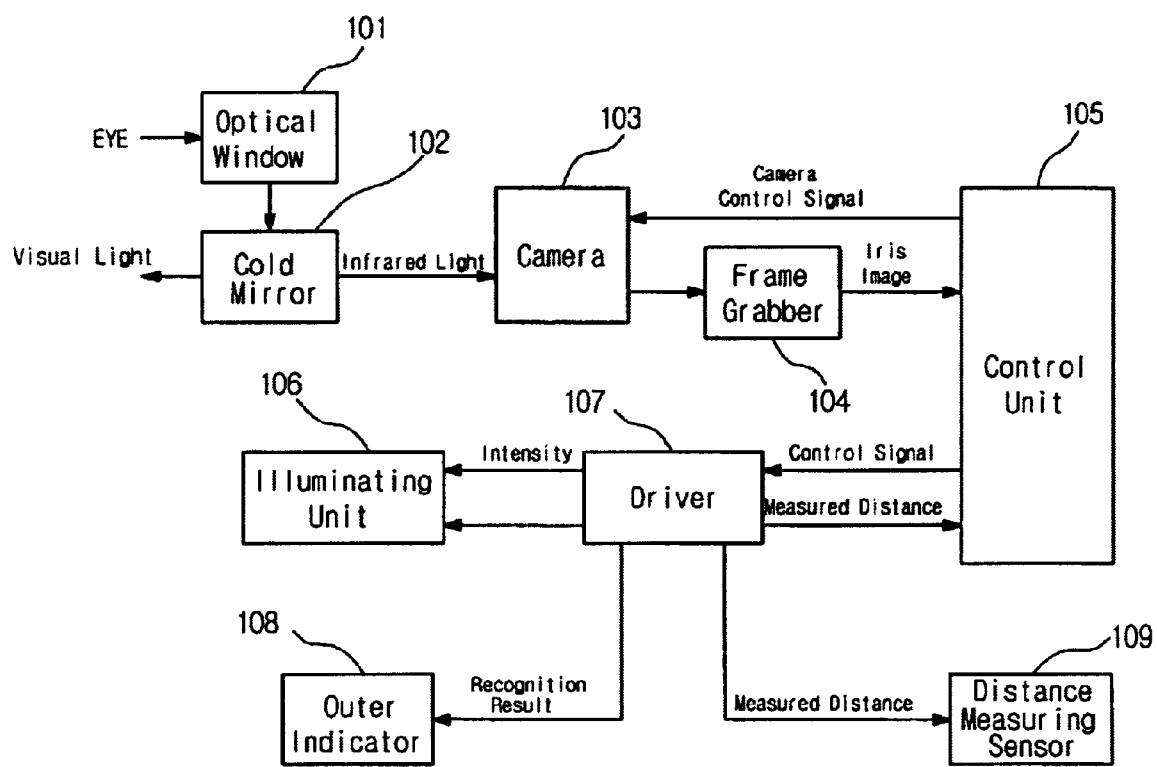
FIG. 1 is a block diagram for showing a configuration of a general iris recognition system.
Figure 2:
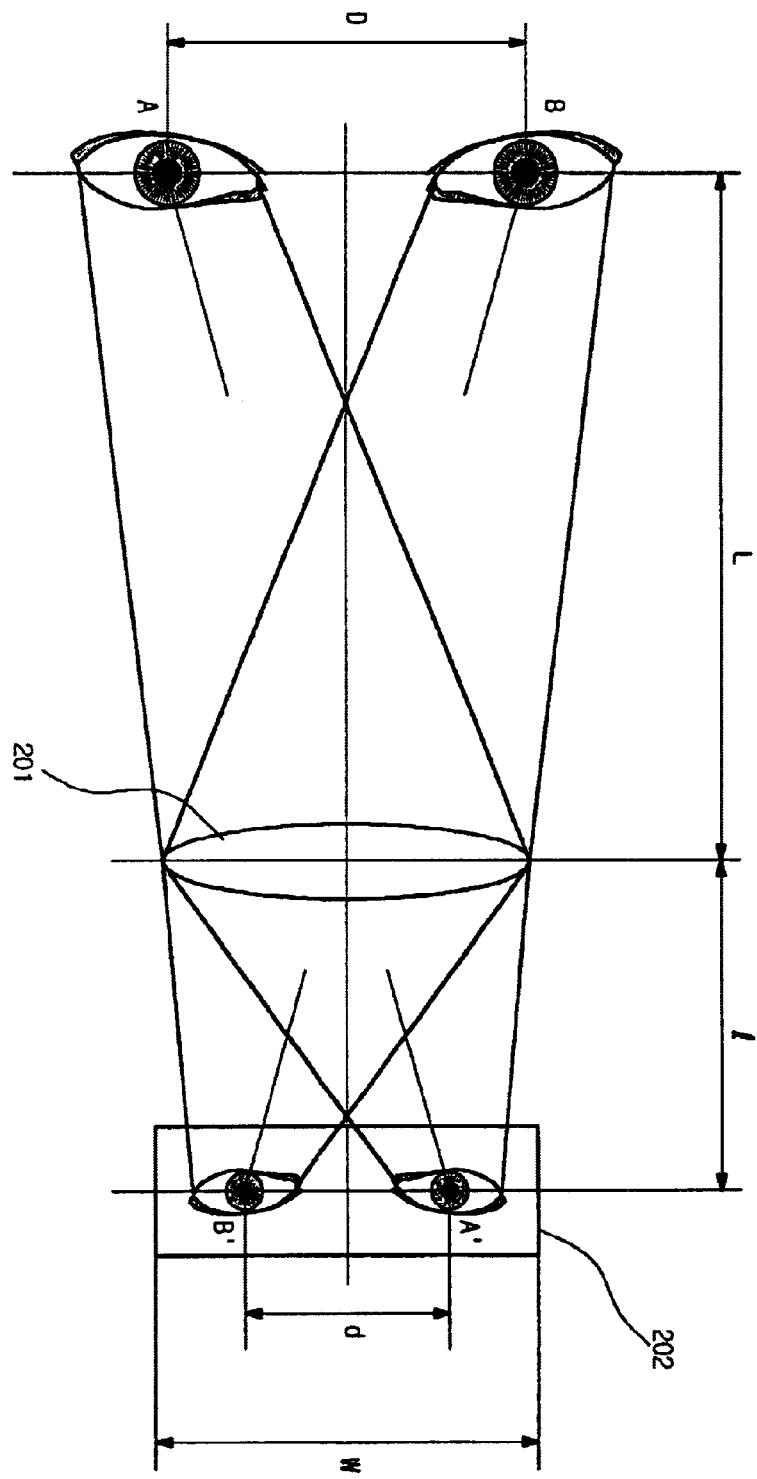
FIG. 2 shows a configuration of an apparatus for directly focusing iris images of both eyes to a camera.

FIG. 2 shows an apparatus for obtaining an image through directly focusing iris images to a CCD. Images of both eyes A and B of a user are obtained as iris images A' and B' in a CCD 202 through a lens 201. In this case, the both eyes A and B are spaced at a certain distance D in practice so that the iris images A' and B' are obtained in the camera as spaced as d according to L/I ratio or lens curvature.

The CCD 202 is a photographing device, which can be used in various forms such as MOS type.

In this case, it is preferable to obtain the iris images as large as possible since a sufficient amount of iris information should be acquired to raise the reliability of iris recognition.

However, in the configuration for directly focusing the images of the both eyes in a simple fashion as in FIG. 2 as a method for acquiring the large iris image like this, the larger the zoom is to obtain the large iris images, the larger the distance d is between the photographed both eyes also. This sometimes requires the iris images to go beyond the CCD area, and accordingly the zoom can be enabled up to such a limitation that the both iris images can be acquired.

Also, when the zoom is made up to the maximum limitation, the ratio of the width W and d of the CCD is always constant in the same user, and this is identically applied to all users.

Meanwhile, considering errors of an optical axis, the zoom is decreased to reduce the ratio of the distance d between the iris images in respect to the CCD width W.

Meanwhile, in the foregoing method, the iris images can be obtained in the same size using the lens 201 even if an operation length L is changed so that the ratio of the distance d between the iris images in respect to the CCD width W can be always maintained constant.

However, when the iris images A' and B' are obtained as in FIG. 2, information in the glabella or between the two eyes is acquired together with the pure iris images used in actual iris recognition. Such glabella information is actually unnecessary for iris recognition and thus can cause a great amount of load to an image process for iris recognition.

Meanwhile, a focusing apparatus using a flat reflector can be considered so as to simultaneously obtain the iris images of the both eyes.

Figure 3:
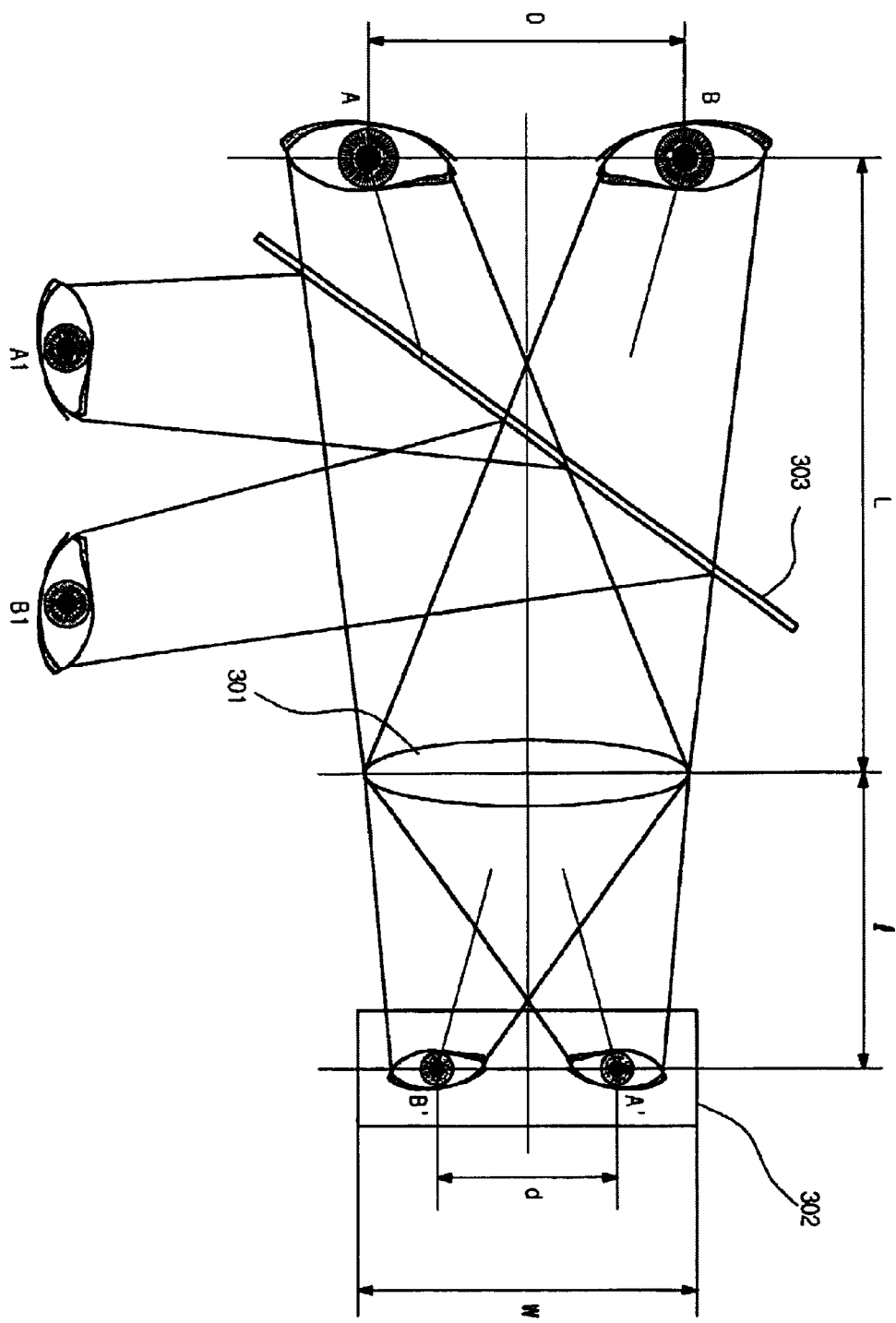
FIG. 3 shows a configuration of an apparatus for focusing iris images of both eyes to a camera using a flat reflector.

FIG. 3 shows an embodiment for obtaining iris images on a CCD 302 through a lens 301 by using a reflector 303 which is inclined for a certain angle. In other words, when the reflector 303 is used, actual eyes A1 and B1 of a user look like placed at A and B.

In this case, however, as described before, when the iris images A' and B' are obtained, information in the glabella or between the two eyes is acquired together with the pure iris images used in actual iris recognition. Such glabella information is actually unnecessary for iris recognition and thus can cause a great amount of load to an image process for iris recognition.

Therefore, a scheme is required for obtaining the iris images of the both eyes through narrowing the distance between the iris images, by which unnecessary information in the glabella can decreased.

In a method of focusing iris images of both eyes comprised of focusing, photographing and authenticating the iris images of the both eyes so as to narrow the distance between the iris images of the both eyes formed on the photographing device as described above, it is proposed an iris recognition method for focusing the iris images of the both eyes, in which lights inputted as the iris images of the both eyes are reflected at angles different to each other to narrow the distance of the incident lights so that the images are formed on the photographing device.

As an apparatus for realizing such a method, it is preferable to realize an apparatus for focusing iris images, which includes iris image focusing means for converting an incident path to narrow the distance between the iris images of the both eyes on an optical path along which the iris images of the both eyes of the user are focused to the camera.

Also, the focusing means can obtain the object thereof by including an angled reflector with one portion being inclined at a certain angle about the center.

Hereinafter more detailed description will be made about the method and apparatus in reference to the drawings as follows.

Figure 4:
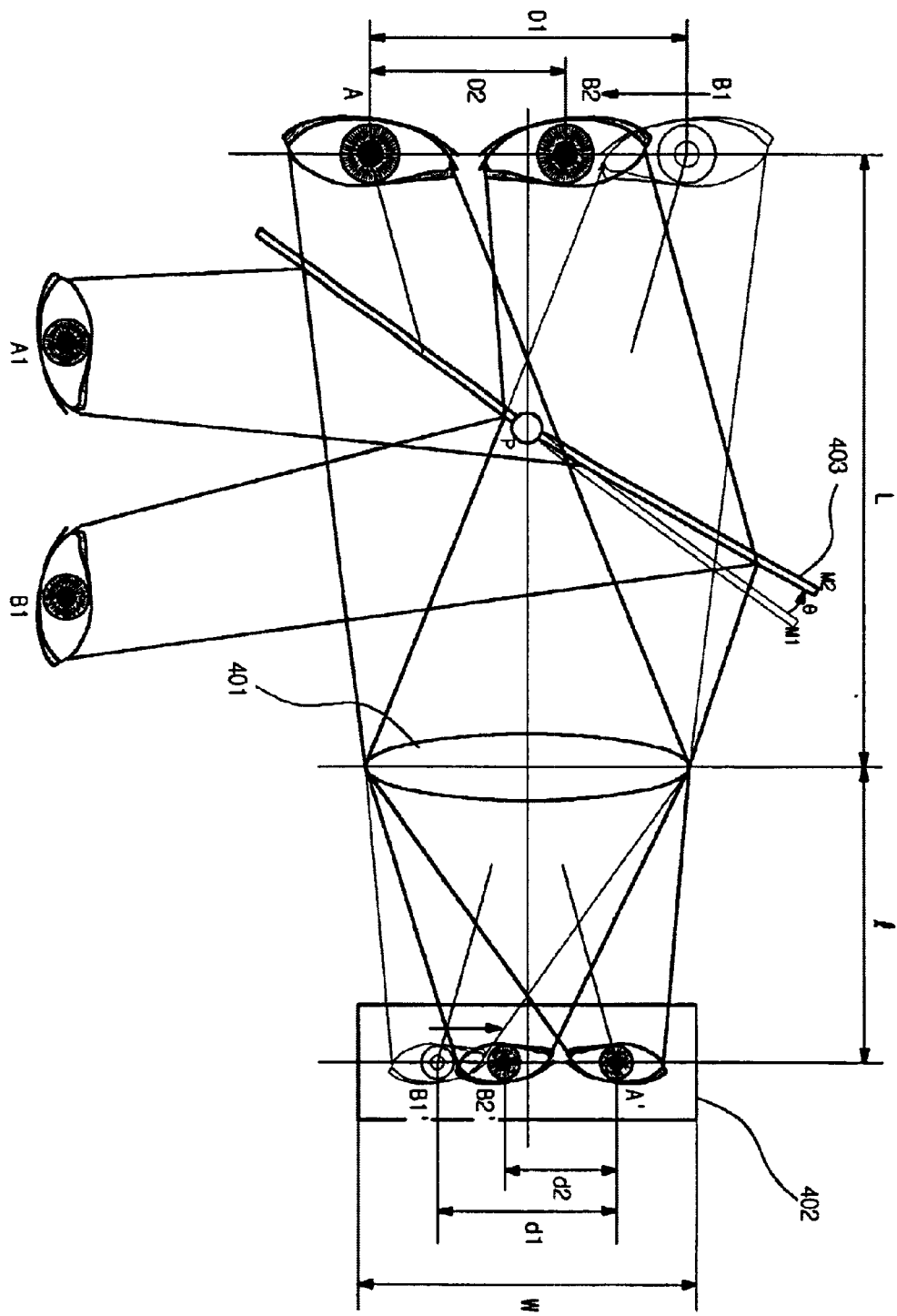
FIG. 4 shows a configuration of an apparatus for focusing iris images of both eyes to a camera using an angled reflector.

FIG. 4 shows an image-focusing unit of the invention, by which the distance between the iris images are narrowed by using a reflector angled at a certain degree so that the iris images of the both eyes can be obtained in larger sizes.

Referring to FIG. 4, the invention includes a reflector 403 inclined at a certain angle about a predetermined position P to set reflection angles different about the both eyes when the iris images of the both eyes are inputted, a lens 401 for refracting the iris images reflected from the reflector 403 and a photographing device 402 for converting optical signals including the iris images into electric signals.

Further, the photographing device preferably employs a CCD, and alternatively can employ various forms such as MOS type.

Further, the reflector 403 is preferably inclined as angled opposite in respect to an incident direction of the iris images so that the iris images can be more adjacent on the photographing device 402.

Also, the reflector 403 may be angled in any direction of right and left about the central position P. Meanwhile, considering that the positions of the images are varied on the photographing device 402 corresponding to the direction, the position of the photographing device 402 can be varied adequately.

Further, the predetermined position P is preferably at the center considering that the iris images of the both eyes are symmetric about the glabella.

Referring to FIG. 4, in order to narrow the length between the iris images of the both eyes formed on the photographing device 402 in particular through the lens 401, the reflector 403 is angled at a certain degree in the foregoing configuration. Also, the reflector 403 is inclined with one side which is angled at a position M1 toward another position M2 about the central position P for a certain degree θ. In other words, the one side where the reflector 403 is inclined is angled counterclockwise.

Meanwhile, when the reflector 403 is inclined with the other side being angled, it is inclined clockwise to the contrary of the one side.

As a result, the invention is characterized in that the reflector is shaped so that the images are formed on the photographing device 402 with the interval to further approach the iris images of the both eyes.

According to the foregoing configuration, when actually both eyes A1 and B1 of a user is reflected by the reflector 403 and then formed on the photographing device 402 through the lens 401, the glabella distance between the iris images is narrowed.

In other words, in comparison that the reflector 403 is not angled as much as the angle θ, actual reflected images of the eyes move from B1 to B2, and accordingly, the iris images are formed at a position as moved from B1' to B2' on the photographing device.

Therefore, the distance between the both iris images of the reflector is shortened from D1 to D2, and resultantly the distance between the iris images on the photographing device is shortened from d1 to d2.

The distance between the iris images is narrowed so that information corresponding to the glabella of the iris images of the both eyes can be acquired in a reduced amount. In other words, since the image corresponding to the glabella can be removed, information about the pure iris images of the both eyes can be acquired in a relatively greater amount.

Further, the distance between the both irises about the width W of the photographing device 402 is shortened to d2, and thus the zoom can be executed in a correspondingly high level to obtain the iris images which has a sufficient size for filing the photographing device.

The foregoing technique provides a basis capable of enlarging the size of the both iris images, and thus iris information can be obtained in a greater amount from the both eyes so that an error rate in iris recognition can be reduced.

The invention enables the distance between the two eyes or the distance between the iris images formed on the photographing device to be reduced in the iris recognition system using the both eyes thereby acquiring iris images in correspondingly larger sizes.

This enables iris information to be acquired in a sufficient amount.

Further, glabella information unnecessary for iris recognition can be reduced to lower the data process load of an iris pattern.

Further, iris information can be obtained in a sufficient amount to lower the error rate of an instrument thereby raising performance and reliability of the iris recognition system using the both eyes.

What is claimed is:

1. An apparatus for focusing iris images of both eyes in a system which executes iris recognition by using the iris images of the both eyes of a user, the apparatus comprising: iris image focusing means for changing propagation directions of the iris images by different amounts, so as to reduce a distance between the iris images of both eyes at a detector.

2. The apparatus for focusing iris images of both eyes according to claim 1, wherein said focusing means includes an angled reflector with one side being inclined at an angle about the center.

3. An apparatus for focusing iris images of both eyes comprising:

a reflector inclined at an angle about a reference position for setting the iris images of the both eyes with reflection angles different with each other when the iris images of the both eyes are inputted;

a lens for refracting the iris images reflected from said reflector; and a photographing device for converting optical signals which contain the iris images into electric signals.

4. The apparatus for focusing iris images of both eyes according to claim 3, wherein said photographing device is an MOS.

5. The apparatus for focusing iris images of both eyes according to claim 3, wherein said photographing device is a CCD.

6. The apparatus for focusing iris images of both eyes according to claim 3, wherein at least one side of the said reflector is inclined as angled opposite to a direction along with the iris images of the both eyes are inputted for approaching the iris images of the both eyes formed on said photographing device.

7. The apparatus for focusing iris images of both eyes according to claim 3, wherein the reference position is the center of said reflector.

8. A method for recognizing iris images of both eyes comprising the following step of: reflecting lights inputted as the iris images of both eyes at different angles for narrowing a distance between the iris images at a detector, wherein all of the iris images of the both eyes are used in user authentication, through focusing, photographing and authentication, whereby the distance between the iris images of the both eyes formed on a photographing device is narrowed.

9. A system for simultaneously imaging left and right irises onto a detector, comprising:

relay optics for simultaneously directing left and right iris optical signals to the detector;

wherein the relay optics alter propagation directions of the left and right iris optical signals by different amounts, so as to reduce a distance between left and right iris images formed at the detector.

10. The system of claim 9, wherein the relay optics comprise a reflector.

11. The system of claim 10, wherein the reflector comprises:
- a first reflective surface for reflecting the left iris optical signal towards the detector at a first reflection angle; and
- a second reflective surface for reflecting the right iris optical signal towards the reflector at a second reflection angle;

wherein the first and second reflection angles are different.

12. The system of claim 10, wherein the relay optics further comprise a lens positioned to receive optical signals reflected from the reflector.

13. The system of claim 9, wherein the propagation directions are altered such that the left and right iris images are positioned immediately adjacent to one another at the detector.

* * * * *